(12) United States Patent
Osei et al.

(10) Patent No.: US 6,533,484 B1
(45) Date of Patent: Mar. 18, 2003

(54) SOLUTION APPLICATOR

(75) Inventors: Johnson Osei, Arlington Heights, IL (US); Jerry Newbrough, Zion, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/952,338

(22) Filed: Sep. 13, 2001

(51) Int. Cl.[7] .................................................. B43K 5/00
(52) U.S. Cl. ..................... 401/205; 401/132; 401/133; 401/265; 401/196; 222/541.1
(58) Field of Search ................................ 401/205, 196, 401/132, 133, 261, 263, 265; 222/631, 476, 541.1, 541.6, 541.7, 541.8

(56) References Cited

U.S. PATENT DOCUMENTS

| | | | |
|---|---|---|---|
| 1,826,195 A | * 10/1931 | Wooldridge | 401/133 |
| 3,184,782 A | * 5/1965 | Armour | 401/263 |
| 3,481,676 A | 12/1969 | Schwartzman | |
| 3,757,782 A | 9/1973 | Aiken | 128/269 |
| 3,847,151 A | * 11/1974 | D'Alessandro et al. | 401/133 |
| 4,057,060 A | 11/1977 | Roth | 128/232 |
| 4,415,288 A | 11/1983 | Gordon et al. | 401/132 |
| 4,498,796 A | 2/1985 | Gordon et al. | 401/132 |
| 4,747,720 A | * 5/1988 | Bellehumeur et al. | 401/205 |
| 4,799,815 A | 1/1989 | Barabino et al. | 401/132 |
| 4,867,326 A | 9/1989 | O'Meara | 215/250 |
| 4,898,293 A | 2/1990 | Morel | 215/250 |
| 4,925,327 A | 5/1990 | Wirt | 401/205 |
| 4,976,379 A | 12/1990 | Sloan | 222/83 |
| 5,042,690 A | 8/1991 | O'Meara | 222/83 |
| 5,120,301 A | 6/1992 | Wu | 604/3 |
| 5,193,928 A | 3/1993 | Balzer et al. | 401/132 |
| 5,288,159 A | 2/1994 | Wirt | 401/133 |
| 5,308,180 A | 5/1994 | Pournoor et al. | 401/205 |
| 5,435,660 A | 7/1995 | Wirt | 401/135 |
| 5,445,462 A | 8/1995 | Johnson et al. | 401/132 |
| 5,487,726 A | 1/1996 | Rabenau et al. | 604/46 |
| 5,658,084 A | 8/1997 | Wirt | 401/132 |
| 5,713,843 A | 2/1998 | Vangsness | 604/3 |
| 5,769,552 A | 6/1998 | Kelley et al. | 401/132 |
| 5,772,346 A | 6/1998 | Edwards | 401/132 |
| 5,791,801 A | 8/1998 | Miller | 401/132 |
| 5,916,882 A | 6/1999 | Jeng | 514/57 |
| 5,927,884 A | 7/1999 | Kao | 401/132 |
| 5,989,205 A | 11/1999 | Pond et al. | 604/3 |

FOREIGN PATENT DOCUMENTS

| WO | WO 99/63934 | 12/1999 |
|---|---|---|

* cited by examiner

*Primary Examiner*—David J. Walczak
(74) *Attorney, Agent, or Firm*—Michael D. Steffensmeier; Andrew G. Rozycki

(57) ABSTRACT

A solution applicator comprising a solution container having a frangible twist-off member that enables solution in the solution container to flow out of the solution container when the twist-off member is twisted. The solution applicator also comprises an applicator head having a proximal end and a distal end and a solution pathway extending from the proximal end to the distal end, the applicator head being engaged with said solution container at the proximal end, the applicator head having an aperture and applicating material at the distal end, and the applicator end having a receiving member that the twist-off member engages when the applicator is rotated relative to the solution container to thereby open the solution container at the twist-off member to enable fluid to flow from the solution container to the applicating material. The solution applicator of the present invention is novel in that it includes a twist-off member that retains solution in the solution container until the solution container and the applicator head are rotated relative to each other to thereby cause the twist-off member to be twisted to allow solution to be applied.

35 Claims, 11 Drawing Sheets

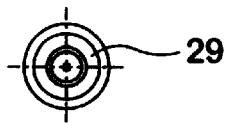
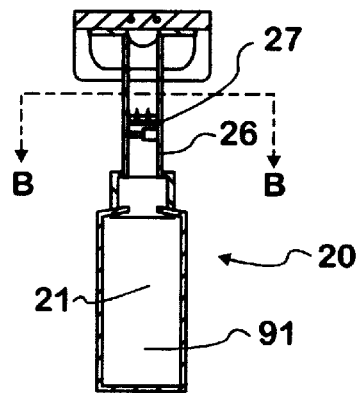
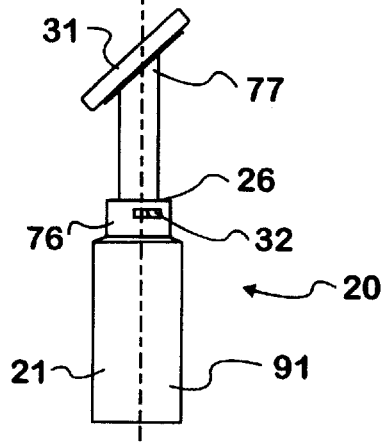
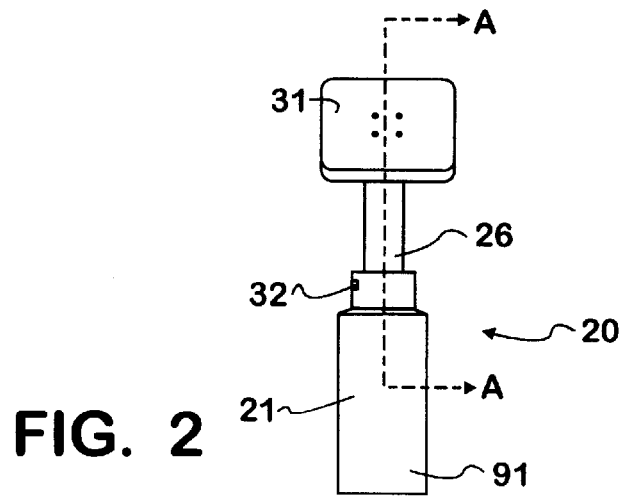
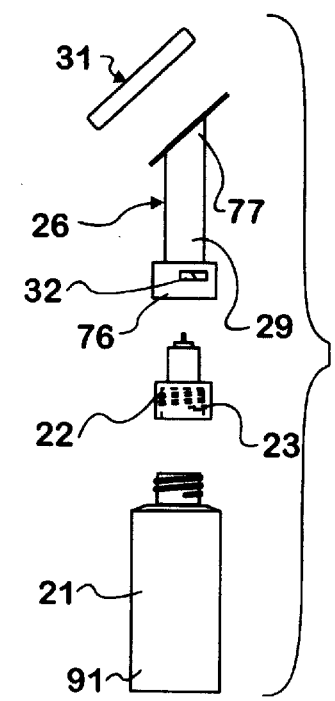

FIG. 4C
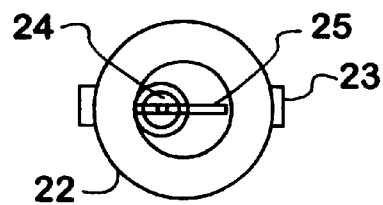
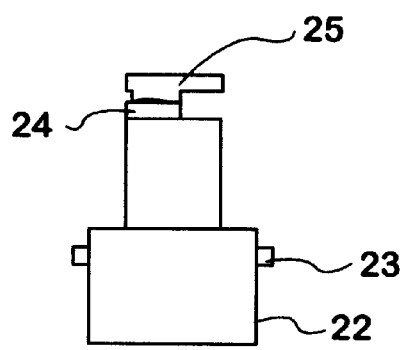
FIG. 4
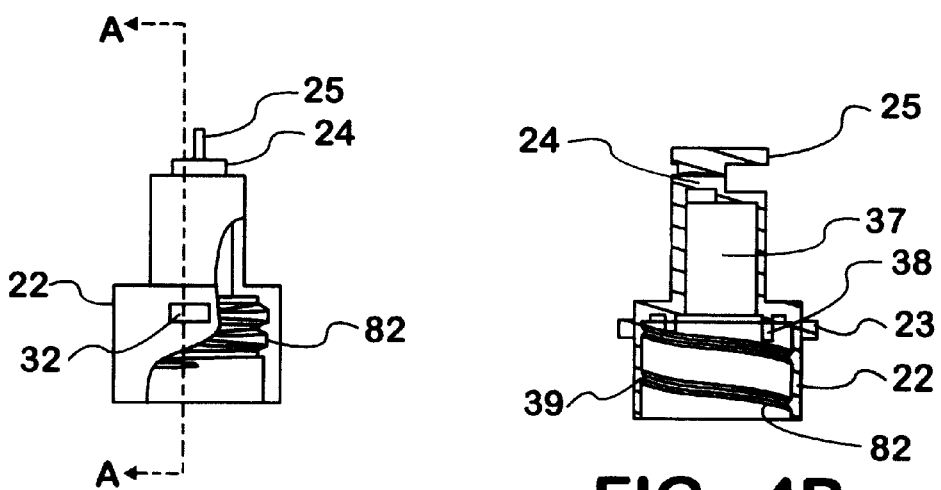
FIG. 4A  FIG. 4B

SOLUTION APPLICATOR

FIELD OF THE INVENTION

The present invention generally relates to solution applicators and, more specifically, to solution applicators for applying antimicrobial solution to skin before surgery.

BACKGROUND AND SUMMARY OF THE INVENTION

Antiseptic preparation of patients for surgery typically includes applying antimicrobial solution to the patient's skin and scrubbing the affected area. There are a number of ways that these antimicrobial solutions are applied from the basic method of dipping a sponge or piece of cotton in an open dish of antimicrobial solution and applying the solution to the patient's skin to more complex, hand-held solution applicators.

There are a number of solution applicators that use spikes and other sharp members that puncture a cartridge or container that contains antimicrobial solution. In many of these types of solution applicators, the cartridge or container is moved longitudinally relative to the spike which then punctures the container to let the solution flow from the container to a sponge on the end of the applicator. These types of solution applicators can rupture during shipping, if the applicator is dropped or sufficient pressure is exerted onto one end of the applicators to thereby force the spike into the solution container, which can inadvertently or accidentally rupture the container and cause the solution to flow out of the container. Some examples of solution applicators using spikes are U.S. Pat. Nos. 4,415,288; 4,498,796; 5,120,301; and 5,769,552.

There are other solution applicators that involve the use of pressure to break or rupture an ampoule inside the applicator by squeezing the sides of the ampoule together. Other solution applicators require bending of an ampoule to break it or pushing an ampoule forward against a member which then bends the ampoule to break it, thereby releasing the solution so that it can then be applied. These types of solution applicators also have problems with breakage during shipping, when dropped, or inadvertently by a user that causes the compartment or ampoule inside of the solution applicator to rupture and thereby release the fluid solution when it is not desired. Some examples of these types of patents discussed above include U.S. Pat. Nos. 3,757,782; 5,288,159; 5,308,180; 5,435,660; 5,445,462; 5,658,084; and 5,927,884.

There is a need for a novel solution applicator that will not easily break during shipment, when dropped, or inadvertently by a user prior to desired use of the solution applicator. The present invention meets these needs. The present invention is a novel solution applicator comprising a solution container having a frangible twist-off member that enables solution in the solution container to flow out of the solution container when the twist-off member is twisted. The solution applicator also comprises an applicator head having a proximal end and a distal end and a solution pathway extending from the proximal end to the distal end, the applicator head being engaged with the solution container at the proximal end, the applicator head having an aperture and applicating material at the distal end, and the applicator end having a receiving member that the twist-off member engages when the applicator is rotated relative to the solution container to thereby open the solution container at the twist-off member to enable fluid to flow from the solution container through the solution pathway and through the aperture in the applicator head to the applicating material.

The solution applicator of the present invention is novel in that it includes a twist-off member that retains solution in the solution container until the solution container and the applicator head are rotated relative to each other to thereby cause the twist-off member to be twisted to create an opening in the solution container that allows solution to be applied. The present invention overcomes the difficulties of the prior art inventions in that it is highly unlikely that during shipment, when dropped or inadvertently by a user, the solution container would be rotated relative to the applicator head. This is a key feature of the present invention. Inadvertent openings of solution applicators usually occur if they are dropped or jammed or bent, so the twisting action required to open the solution applicator of the present invention is a very beneficial feature and superior to the prior art inventions.

Various objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a front view of an embodiment of the solution applicator in accordance with the present invention.

FIG. 2A is a side view of an embodiment of the solution applicator in accordance with the present invention.

FIG. 2B is an assembly view of an embodiment of the solution applicator in accordance with the present invention.

FIG. 2C is a cross-sectional view of an embodiment taken along line A—A in FIG. 2A in accordance with the present invention.

FIG. 2D is a cross-sectional view of an embodiment taken along line B—B in FIG. 2C in accordance with the present invention.

FIG. 4 is a side view of a portion of the solution container of an embodiment of the solution applicator in accordance with the present invention.

FIG. 4A is a cut-away view of the embodiment shown in FIG. 4.

FIG. 4B is a cross-sectional view of an embodiment taken along line A—A in FIG. 4A in accordance with the present invention.

FIG. 4C is a top view of the embodiment shown in FIG. 4.

DETAILED DESCRIPTION OF THE PREFERRED EMBODIMENTS

Figure 1:
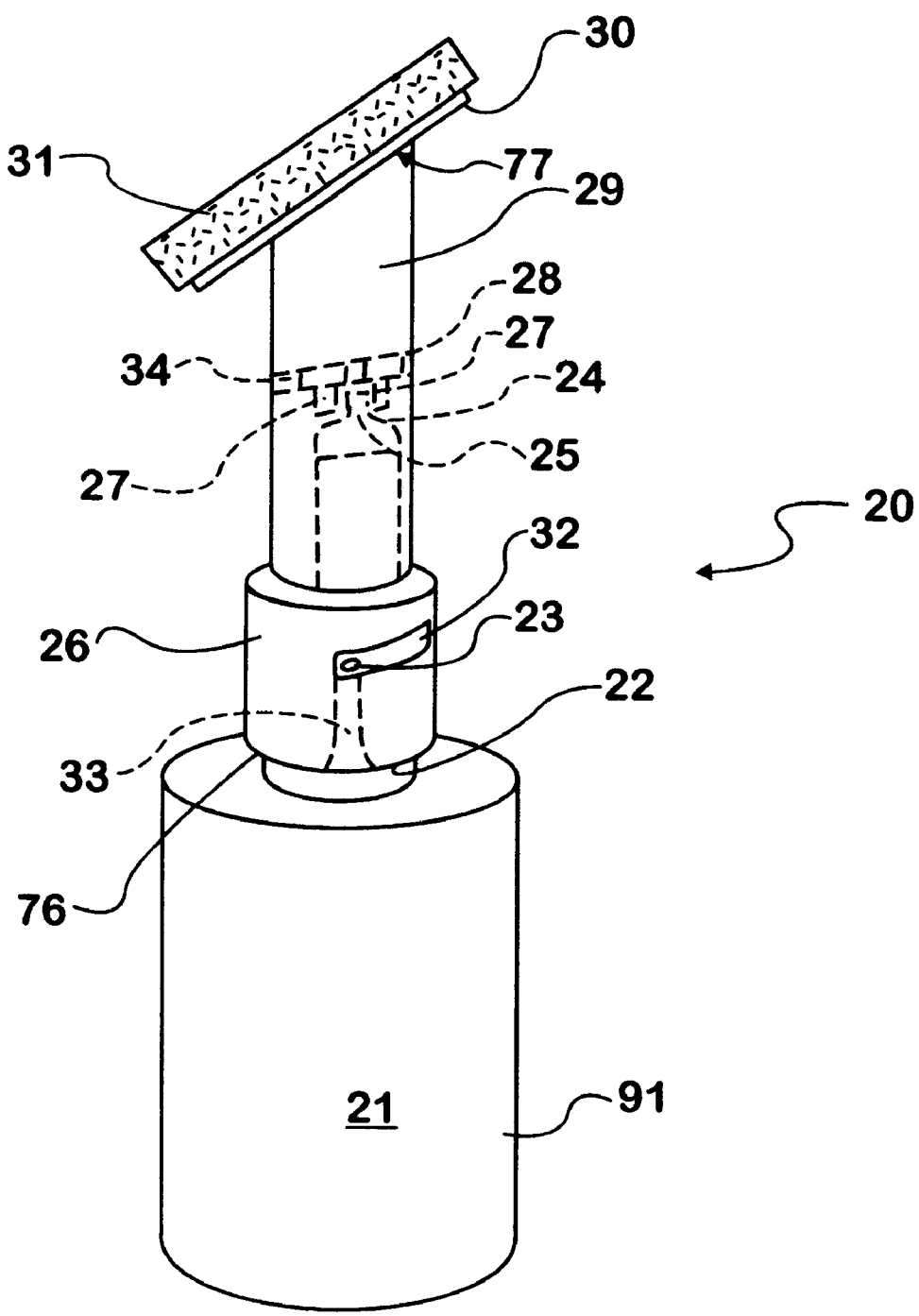
FIG. 1 is a perspective view of an embodiment of the solution applicator in accordance with the present invention.

The detailed embodiments of the present invention are disclosed herein. It should be understood, however, that the enclosed embodiments are merely exemplary of the invention, which may be embodied in various forms. Therefore, the details disclosed herein are not to be interpreted as limiting, but merely as a basis for teaching one skilled in the art how to make and/or use the invention.

Referring now to the drawings, preferred embodiments of the solution applicator of the present invention are shown in FIGS. 1–13. The solution applicator 20 of the present invention includes a solution container 21 that contains the solution to be applied by the solution applicator 20. The solution may be various types of liquids or gels to be applied on a surface, but the present invention is very useful for antimicrobial solutions applied to patients before surgery. The solution container 20 is self-contained in that no other implements, techniques or tools are necessary for accessing and applying the solution.

The solution container 21 may be shaped like a cylindrical bottle or shaped like other types of reservoirs or containers that hold solution. The solution container 21 includes a frangible, twist-off member 25 that enables solution in the solution container 21 to flow out of the solution container 21 when the twist-off member 25 is twisted to thereby provide an opening through which solution in the solution container 21 may flow. The twist-off member 25 may also be a type of twist-to-break member that will not actually twist off completely, but will break enough so that an opening will be created to allow the solution in the solution container 21 to flow out of the solution container 21. This enables solution to be available for application by the solution applicator 20.

The solution container 21 may include a cap 22 that is either integrally formed as part of the solution container 21 or the cap 22 may be designed for threaded connection to threads on the container portion 91 of the solution container 21 to thereby form a sealed solution container 21 to hold the solution. In this embodiment, the cap 22 would have the twist-off member 25 integrally formed as part of the cap 22.

As shown in FIGS. 1, 2, 2A, 2B, 2C, 2D and 3, the solution applicator 20 includes an applicator head 26 engaged with the solution container 21. The applicator head 26 has a proximal end 76 and a distal end 77 and a solution pathway 29 that extends from the proximal end 76 to the distal end 77. Solution pathway 29 may be a tube, duct, channel, lumen, wick or other type of pathway through which liquids can flow. This solution pathway 29 allows solution to flow from the solution container 21 (when the twist-off member 25 is twisted to create an opening in the solution container 21) and then to be able to flow through orifices/apertures 78 (see FIG. 6) to the applicating material 31.

The applicating material 31 includes any type of material that will absorb the solution and allow the solution to be applied to a surface (e.g., a patient's skin). A suitable applicating material 31 for a solution applicator 21 is foam sponge, but many other suitable applicating materials 31 (such as cotton swabs, pads, etc.) that are porous and can retain and distribute solution may be used. It is preferable if the applicating material 31 allows the solution to flow into the applicating material 31, but does not allow the liquid solution to drip from the porous applicating material 31. Flat surface 30 provides a mounting surface to which the applicating material 31 is attached. The flat surface 30 has apertures 78 therethrough in order to allow the solution to get to the applicating material 31 from the solution pathway 29.

Applicator head 26 may also have a slot 32 near the proximal end 76 that is engaged by a locating pin 23 that protrudes outwardly from the cap 22 of the solution container 21 to ensure proper orientation of the applicator head 26 as it is coupled to cap 22 of the solution container 21. Locating pin 23 engages slot 32 to provide a means to retain the engagement of applicator head 26 onto cap 22 of the solution container 21 after assembly. Applicator head 26 has a receiving member 27 that forms an area that cooperates with twist-off member 25 such that when the applicator head 26 is rotated relative to the solution container 21, the receiving member 27 will tear or break the twist-off member 25, which opens the solution container 21 and enables solution to flow from the solution container 21. The receiving member 27 can be formed in many suitable ways (including a tongue-and-groove arrangement), as long as it will engage and tear the twist-off member 25 when the applicator head 26 is rotated relative to the solution container 21.

Figure 3:
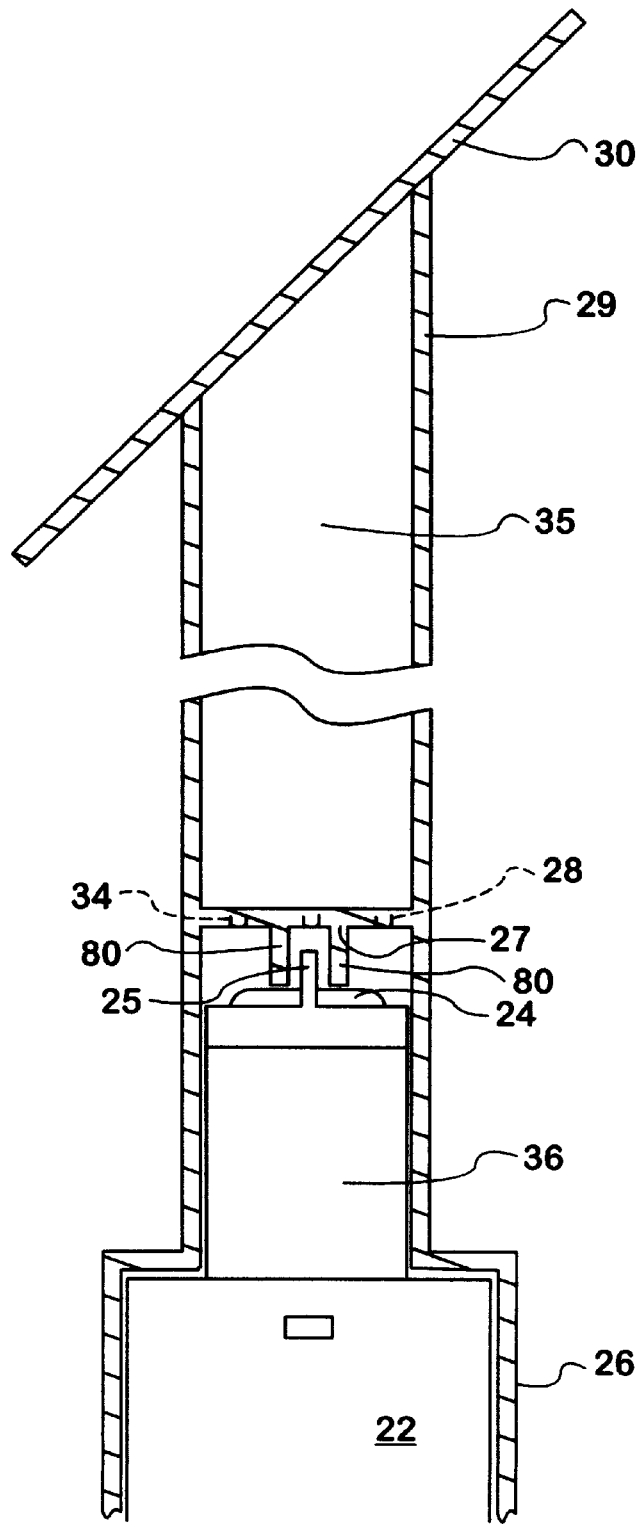
FIG. 3 is a cross-sectional view of a portion of an embodiment taken along line A—A in FIG. 2 in accordance with the present invention.
Figure 6:
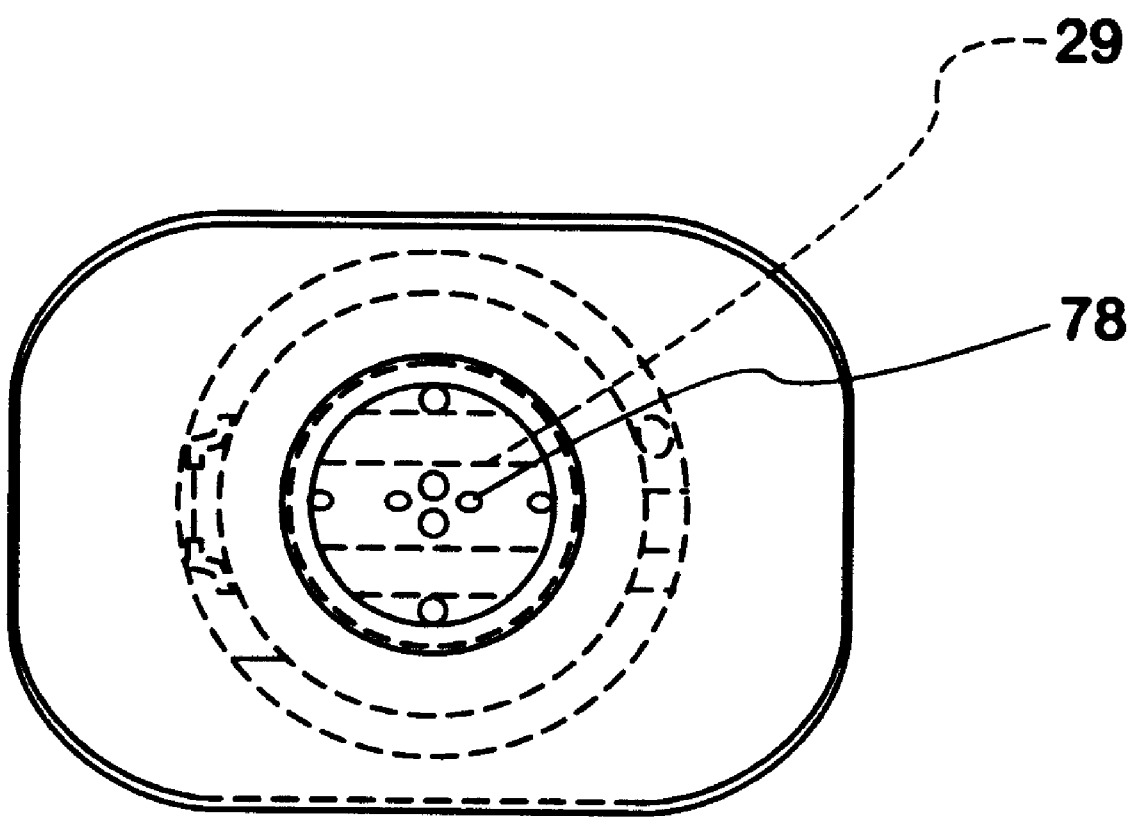
FIG. 6 is a top view of the applicator head without the applicating material of the embodiment of the solution applicator in accordance with the present invention.
Figure 7:
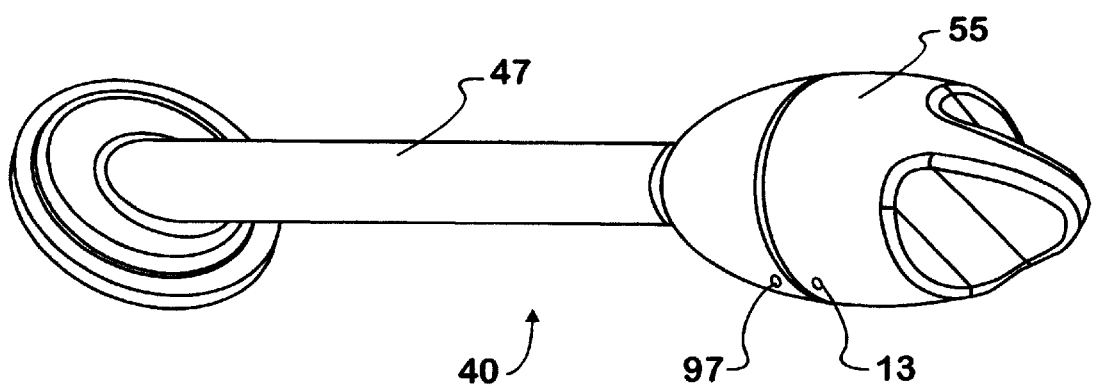
FIG. 7 is a perspective view of another embodiment of the solution applicator in accordance with the present invention.
Figure 8:
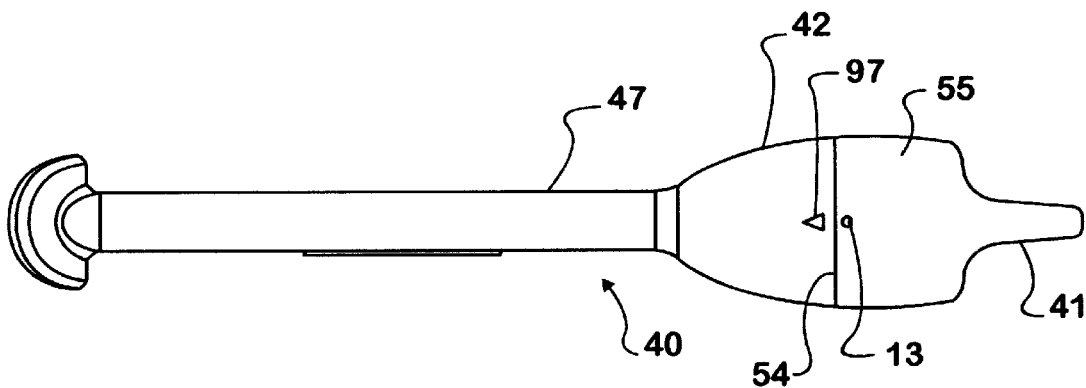
FIG. 8 is a top view of an embodiment of the solution applicator shown in FIG. 7 in accordance with the present invention.

A preferred embodiment of the receiving member 27 is shown in FIG. 3, in which the receiving member 27 includes two parallel members 80 attached to a cross member 28 that extends across the solution pathway 29 of the applicator head 26. As shown in FIG. 3, the parallel members 80 capture or mate with a portion of the twist-off member 25 and when the applicator head 26 is rotated relative to the solution container 21, the twist-off member 25 is torn to provide an opening in the solution container 21 at the frangible portion 24. Cross member 28 extends across the solution pathway 29 of the applicator head 26 and it can also be designed to be able to control the rate of fluid flow from the solution container 21 to the applicating material 31. As shown in FIG. 6, there may also be apertures 78 that can also control the rate of flow of fluid and uniform distribution of solution to the applicating material 31 In a preferred embodiment, there are holes or apertures 34 through the receiving member 27 which are of sufficient size to allow enough solution to pass through the receiving member 27 to the applicating material 31 and also are of small enough size so that there is not too much solution going to the applicating material 31.

Figure 5:
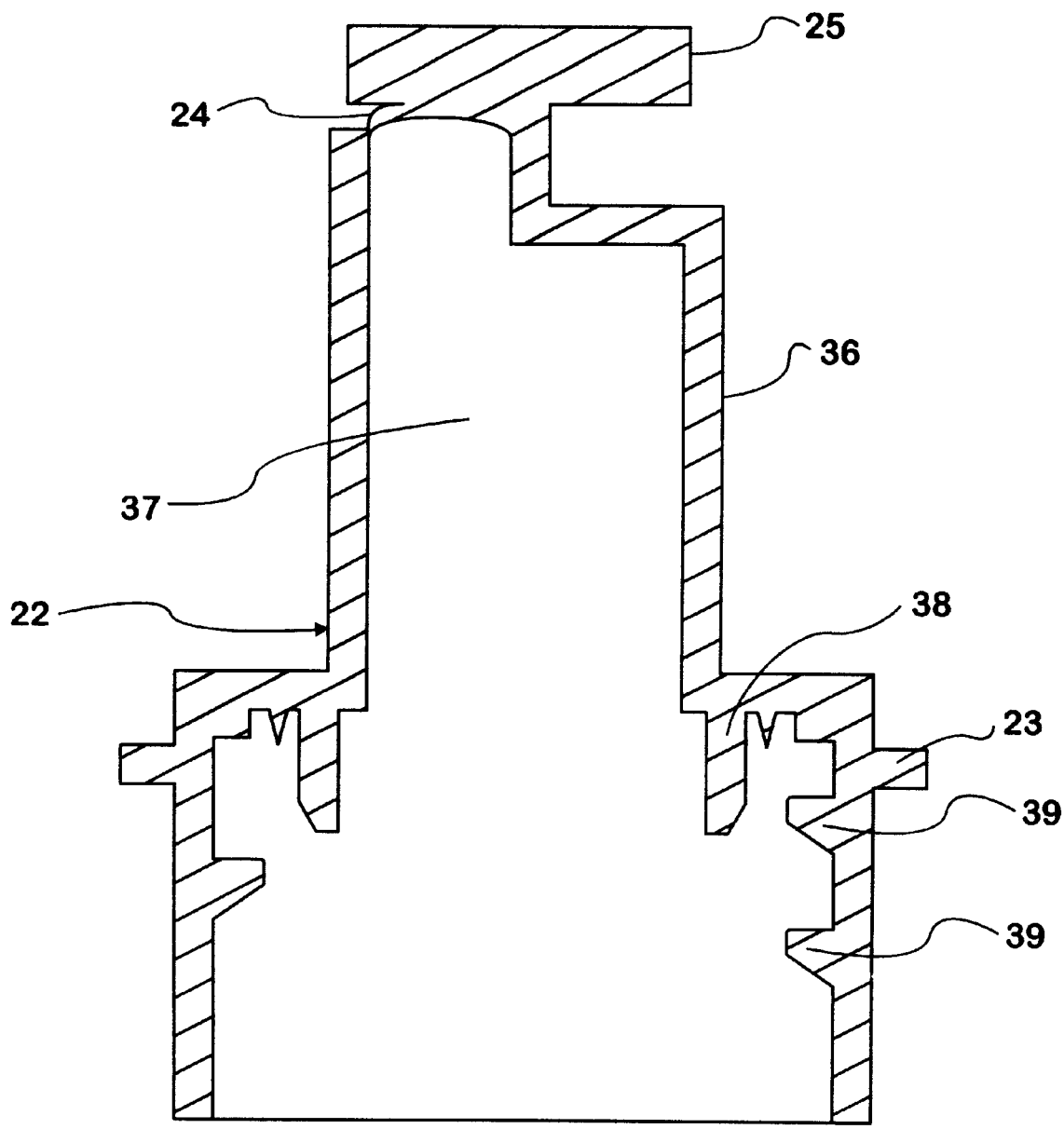
FIG. 5 is a cross-sectional view of a portion of the solution container of an embodiment (without the threads) taken along line A—A in FIG. 4A in accordance with the present invention.

FIGS. 4B and 5 show a portion of the solution container 21 with the twist-off member 25, frangible area 24 and fluid path 37 (which is shown as the interior of the portion 36 that carries fluid from the container portion 91 of the solution container 21 to the frangible area 24). For the embodiments in which the cap 22 is threaded to the container portion of the solution container 21, protruding portion 38 forms a seal with the container portion 91 of solution container 21 to prevent leakage prior to the activation of the solution applicator 20. Threads 39 engage with mating threads 82 of the container portion to lock the cap 22 and the container portion 91 together to form the solution container 21.

Another preferred embodiment of a solution applicator 40 is shown in FIGS. 7–13. The solution applicator 40 includes a solution container 55 having a frangible twist-off member 52 and an applicator head 47 that engages with the solution container 55 such that the frangible twist-off member 52 is torn when the solution container 55 is rotated relative to the applicator head 47. The solution is contained in the solution container 55 which can be formed in various shapes, including the oval-shaped solution container 55 shown in FIGS. 7–9 and 12. The solution container 55 is preferably locked in place to the applicator head 47 by having a lip 96 formed around the circumference of segment 42 of the applicator head 47 which mates with a holding ring 88 (see FIG. 12) that is like a channel around the circumference of the solution container's 55 circumference into which the lip 96 snaps to thereby put the applicator head and the solution container in locking engagement with each other. This lip 96 and channel 88 provide a sealed connection between the applicator head 47 and solution container 55 so that the solution does not escape between the applicator head 47 and solution container 55. The engagement between the lip 96 and channel 88 allow rotation of the applicator head 47 relative to the solution container 55, so that the twist-off member 52 can be torn to create an opening to allow solution to flow from the solution container 55 to the applicating material 65 on the end of the applicator head 47.

Figure 10:
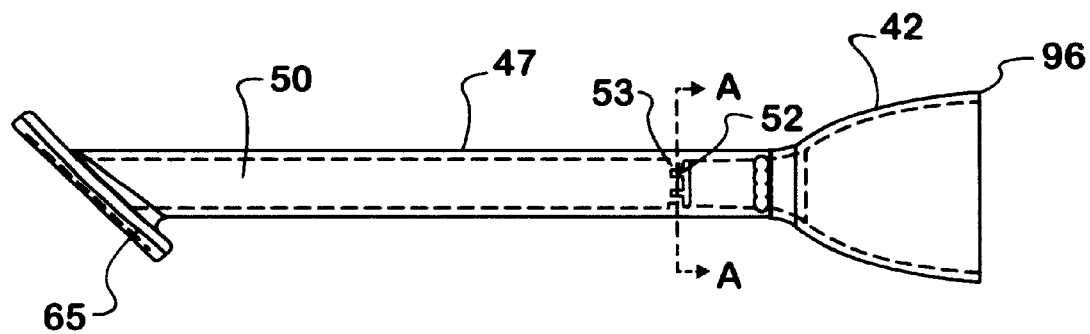
FIG. 10 is a side view of a portion of an embodiment of the applicator head in accordance with the present invention.
Figure 10A:
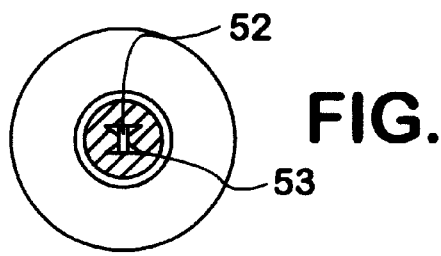
FIG. 10A is a cross-sectional view of an embodiment taken along line A—A in FIG. 10 in accordance with the present invention.
Figure 10B:
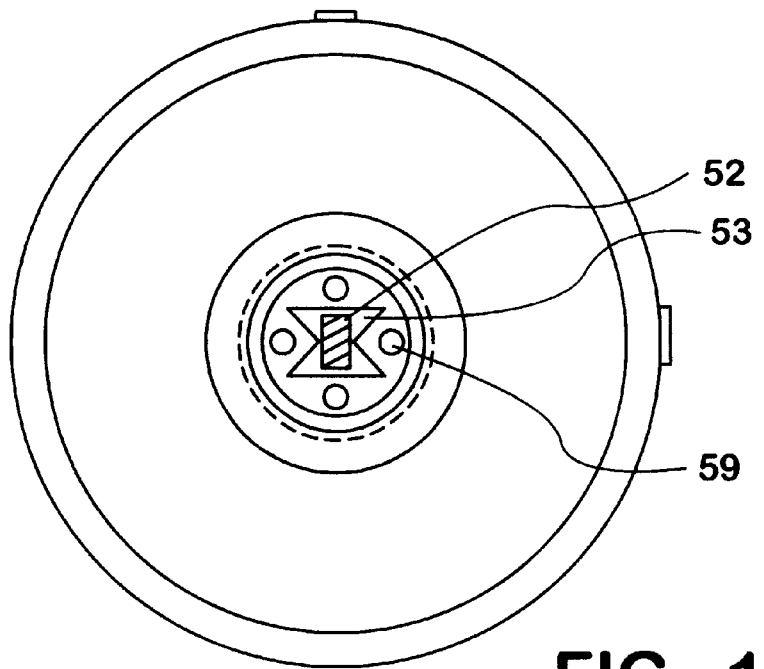
FIG. 10B is a cross-sectional view of another embodiment taken along line A—A in FIG. 10 in accordance with the present invention.

The applicator head 47 has a receiving member 53 (as shown in FIGS. 10, 10A and 10B) that receives the twist-off member 52 such that twisting of the applicator head 47 (and therefore receiving member 53) relative to the solution container 55 (and therefore twist-off member 52) will cause the twist-off member 52 to tear an opening in the solution container 55 to thereby allow solution to flow from the solution container 55 into the applicator head 47. The receiving member 53 also may have apertures 59 therethrough that help control the flow of fluid past and through the receiving member 53 so that the solution can flow to the applicating material 65. The solution applicator 40 may also contain indicia 13, 97 which indicate to the user that the user needs to rotate the applicator head 47 relative to the solution container 55 such that the indicia 13, 97 are aligned, which is a signal to the user that the twist-off member 52 has been twisted enough to break it so that there is an opening in the solution container 55 to release the solution into the applicator head 47. Indicia 13, 97 may be holes, markings, words, protrusions and various other suitable types of indicia that will enable a user to know when the rotation has been sufficient to tear or break the twist-off member 52. Solution container 55 may also be squeezable so that a user can squeeze the solution container 55 to increase the flow of solution to the applicator head 47.

The parts of the solution applicator 40 may be made of numerous types of plastic materials including high density polyethylene, polypropylene, low density polyethylene or polyvinyl chloride (PVC). The solution container 55 preferably has a grip portion 41 that a user can easily grasp the solution container 55 to rotate it relative to the applicator head 47.

Figure 12:
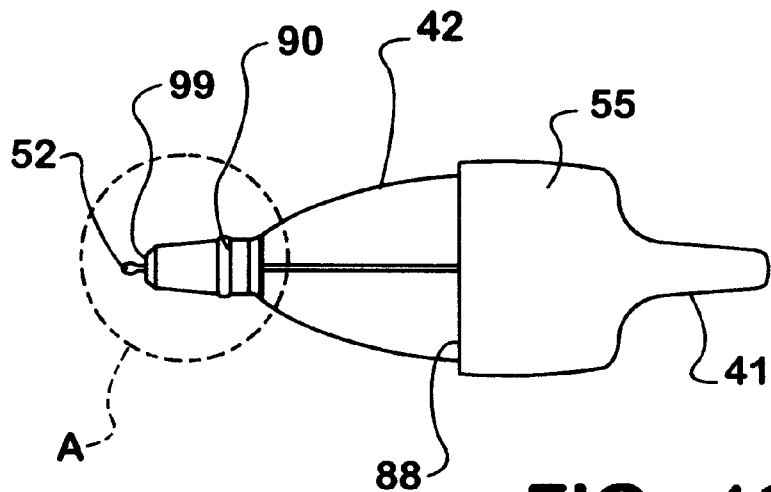
FIG. 12 is a side view of an embodiment of the solution container in accordance with the present invention.
Figure 12A:
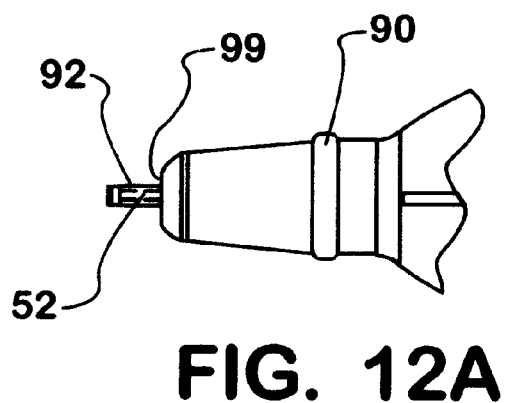
FIG. 12A is a blown up view of the twist-off element and end of the solution container shown in FIG. 12 in accordance with the present invention.
Figure 13:
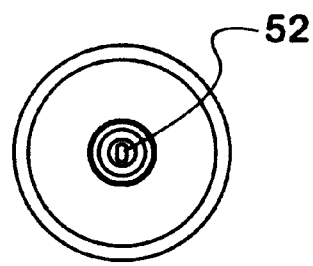
FIG. 13 is an end view of the solution container shown in FIG. 12 in accordance with the present invention.

In another preferred embodiment, the twist-off member 52 may also have a retainer mechanism 92 as shown in FIG. 12A that allows the twist-off member 52 to slide into the receiving member 53 and then the retainer mechanism 92 expands such that the twist-off member 52 cannot be pulled back from the receiving member 53. This helps hold the solution container 55 together with the applicator head 47. In a preferred embodiment, said retainer mechanism 92 is V-shaped with a spring force such that the legs of the V squeeze together when the retainer mechanism 92 and the twist-off member 52 start to be inserted into said receiving member 53. The legs of the V spring apart when said retainer mechanism 92 is fully inserted into said receiving member 53 to thereby hold said applicator head 47 and said solution container 55 together. The retainer mechanism 92 is preferably part of the twist-off member 52. The retainer mechanism 92 can be molded as ribs coming off the end of the break off section of the twist-off member 52, so that after pushing the end part of the solution container that contains the twist-off member 52 into the applicator head 47, the ribs of the retainer mechanism 92 lock in place into the receiving member 53 making it impossible for the applicator head to be removed from the solution container prior to activation (twisting and breaking the twist-off member 52). It is preferable that the retainer mechanism 92 be formed of the same material as that of the twist-off member 52.

Figure 9:
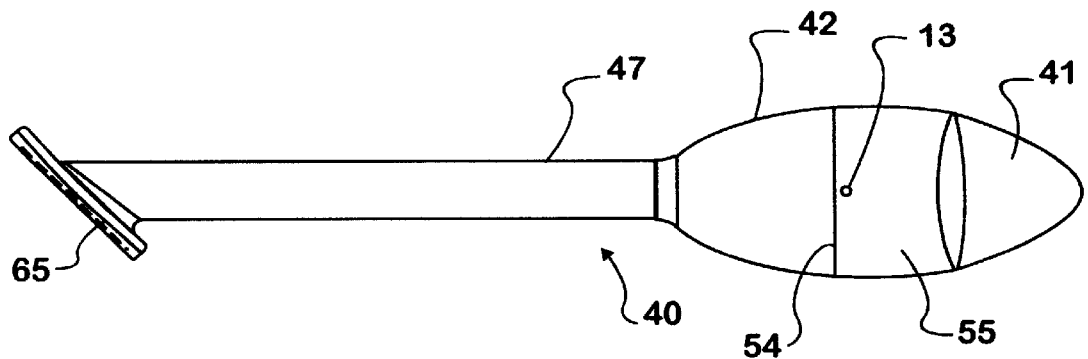
FIG. 9 is a side view of an embodiment of the solution applicator shown in FIG. 7 in accordance with the present invention.
Figure 11:
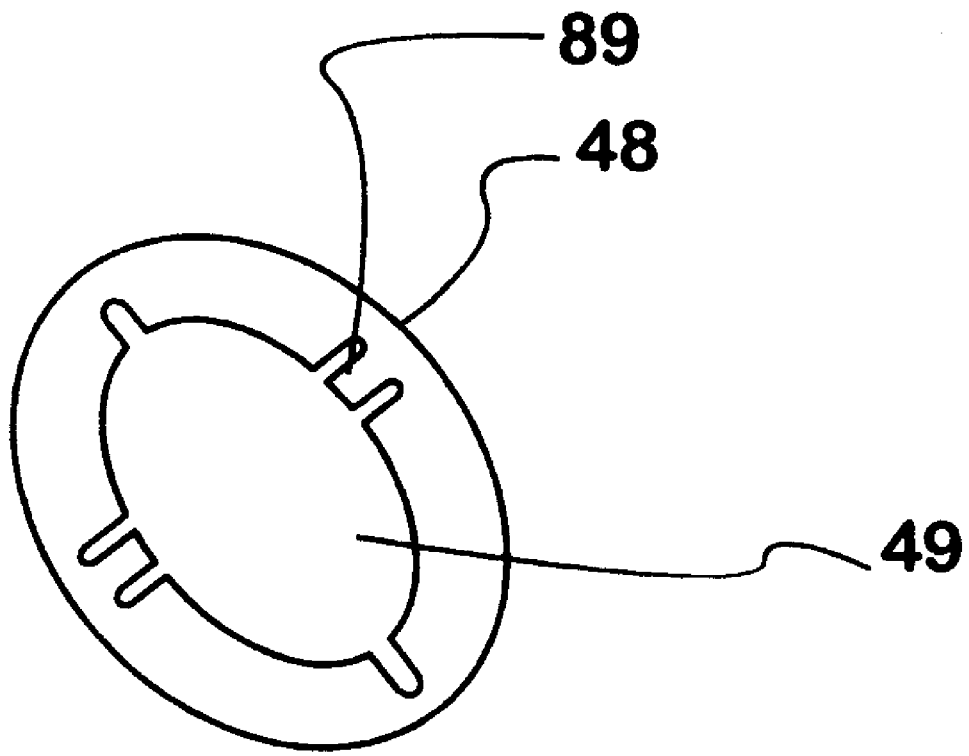
FIG. 11 is an end view of the flat surface of the applicator head of the solution applicator shown in FIG. 7 in accordance with the present invention.

The applicator head 47 preferably has a solution pathway 50 that enables solution to flow from the opening from the torn twist-off member 52 past the receiving member 53 on through the applicator head 47 to the applicating material 65, which is attached to flat end 48 of the applicator head 47. The flat end 48 and the applicating material 65 are preferably formed at an angle as shown in FIGS. 9 and 10 to make them ergonomically designed for the user. The flat end 48 with an orifice 49 therethrough is shown in FIG. 11. The orifice 49 may be of various sizes and could have a number of smaller holes therethrough to obtain a suitable flow rate of the solution to the applicating material 65. The applicating material 65 is attached to the flat end 48 and the flat end 48 may have radial slots 89 to allow solution to flow evenly to the applicating material 65.

The twist-off member 52 is preferably a tab that extends outwardly from the solution container 55 and that is connected to the rest of the solution container 55 by a frangible web 99 that will tear when the tab is twisted off or twisted to break. This frangible web 99 is designed so that when the twist-off member 52 is twisted or rotated, the frangible web 99 will tear open to provide an opening for the solution to flow out of the solution container 55. It is preferable to have the frangible web 99 be somewhat thinner than the walls of the rest of the solution container 55 so that it tears more easily at the location of the frangible web 99. Ring 90 helps retain solution in the applicator head 47 so that it does not get on the user's hands near channel 88.

Having described the invention in detail, those skilled in the art will appreciate that, given the present disclosure, modifications may be made to the invention without departing from the spirit of the inventive concept herein described. Therefore, it is not intended that the scope of the invention be limited to the specific and preferred embodiments illustrated and described. Rather, it is intended that the scope of the invention be determined by the appended claims.

What is claimed is:

1. A solution applicator comprising:
   a solution container having a twist-off member that enables solution in said solution container to flow out of the solution container when said twist-off member is twisted; and an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container at the twist-off member to enable fluid to flow from said solution container through the solution pathway and through the aperture in said applicator head, wherein said twist-off member is connected to the solution container by a frangible web unitary with the twist-off member and said solution container.

2. The solution applicator of claim 1 wherein said solution container has a channel formed around its circumference and said applicator head has a lip formed along the inside of its proximate end, said lip mating with said channel to rotatingly couple said applicator head and said solution container together.

3. The solution applicator of claim 1 wherein said twist-off member of said solution container includes a retainer mechanism that cooperates with said receiving member of said applicator head to couple said applicator head and said solution container together.

4. The solution applicator of claim 3 wherein said retainer mechanism is V-shaped with a spring force such that the legs of the V squeeze together when said retainer mechanism and twist-off member start to be inserted into said receiving member and then the legs of the V spring apart when said retainer mechanism is fully inserted into said receiving member to thereby hold said applicator head and said solution container together.

5. The solution applicator of claim 1 wherein said frangible web is formed of a thinner material than the rest of said solution container so that the frangible web tears to form an opening in said solution container when said receiving member engages the twist-off member and said applicator head is rotated relative to said solution container.

6. The solution applicator of claim 1 wherein said solution container comprises a container portion connected to a cap to form a sealed reservoir of solution inside of said solution container, said cap having the twist-off member.

7. The solution applicator of claim 6 wherein said twist-off member of said solution container includes a retainer mechanism that cooperates with said receiving member of said applicator head to couple said applicator head and said solution container together.

8. The solution applicator of claim 6 wherein said twist-off member is connected to the cap of said solution container by a frangible web unitary with the twist-off member and the cap.

9. The solution applicator of claim 8 wherein said frangible web is formed of a thinner material than the rest of the cap so that the frangible web tears to form an opening in the cap when said receiving member engages the twist-off member and said applicator head is rotated relative to said solution container.

10. The solution applicator of claim 6 wherein said solution container and said applicator head each have indicia thereon, said indicia are positioned so that when they line up upon rotation of said applicator head relative to said solution container, the twist-off member has been torn to create an opening in said solution container.

11. The solution applicator of claim 6 wherein said applicator head includes applicating material.

12. The solution applicator of claim 6 wherein the cap has a locating pin that protrudes outwardly from the cap, and said applicator head has a slot near its proximal end that is engaged by the locating pin to ensure proper orientation of said applicator head as it is coupled to said solution container.

13. The solution applicator of claim 6 wherein said container portion is connected to said cap by mating threads.

14. The solution applicator of claim 1 wherein said solution container and said applicator head each have indicia thereon, said indicia are positioned so that when they line up upon rotation of said applicator head relative to said solution container, the twist-off member has been torn to create an opening in said solution container.

15. The solution applicator of claim 1 wherein said applicator head includes applicating material.

16. The solution applicator of claim 1 wherein said solution container has a locating pin that protrudes outwardly from said solution container, and said applicator head has a slot near its proximal end that is engaged by the locating pin to ensure proper orientation of said applicator head as it is coupled to said solution container.

17. The solution applicator of claim 1 wherein said solution container has a ring thereon that will contact said applicator head near its proximal end so that solution will not flow out of said solution applicator between said applicator head and said solution container.

18. A solution applicator comprising:
    a solution container having a twist-off member that enables solution in said solution container to flow out of the solution container when said twist-off member is twisted, wherein said solution container comprises a container portion connected to a cap to form a sealed reservoir of solution inside of said solution container, wherein said container portion is connected to said cap by mating threads, said cap having the twist-off member; and
    an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container to enable fluid to flow from said solution container through the solution pathway and through the aperture in said applicator head.

19. The solution applicator of claim 18 wherein said solution container has a channel formed around its circumference and said applicator head has a lip formed along the inside of its proximate end, said lip mating with said channel to rotatingly couple said applicator head and said solution container together.

20. The solution applicator of claim 18 wherein said twist-off member is connected to the solution container by a frangible web unitary with the twist-off member and said solution container.

21. The solution applicator of claim 20 wherein said frangible web is formed of a thinner material than the rest of said solution container so that the frangible web tears to form an opening in said solution container when said receiving member engages the twist-off member and said applicator head is rotated relative to said solution container.

22. The solution applicator of claim 18 wherein said solution container has a locating pin that protrudes outwardly from said solution container, and said applicator head has a slot near its proximal end that is engaged by the locating pin to ensure proper orientation of said applicator head as it is coupled to said solution container.

23. A solution applicator comprising:
   a solution container having a twist-off member that enables solution in said solution container to flow out of the solution container when said twist-off member is twisted, wherein said twist-off member of said solution container includes a retainer mechanism that cooperates with said receiving member of said applicator head to couple said applicator head and said solution container together, wherein said retainer mechanism is V-shaped with a spring force such that the legs of the V squeeze together when said retainer mechanism and twist-off member start to be inserted into said receiving member and then the legs of the V spring apart when said retainer mechanism is fully inserted into said receiving member to thereby hold said applicator head and said solution container together; and
   an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container to enable fluid to flow from said solution container through the solution pathway and through the aperture in said applicator head.

24. The solution applicator of claim 23 wherein said twist-off member is connected to the solution container by a frangible web unitary with the twist-off member and said solution container.

25. A solution applicator comprising:
   a solution container having a twist-off member that enables solution in said solution container to flow out of the solution container when said twist-off member is twisted; and
   an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container to enable fluid to flow from said solution container through the solution pathway and through the aperture in said applicator head;
   wherein said solution container and said applicator head each have indicia thereon, said indicia are positioned so that when they line up upon rotation of said applicator head relative to said solution container, the twist-off member has been torn to create an opening in said solution container.

26. The solution applicator of claim 25 wherein said twist-off member is connected to the solution container by a frangible web unitary with the twist-off member and said solution container.

27. The solution applicator of claim 26 wherein said frangible web is formed of a thinner material than the rest of said solution container so that the frangible web tears to form an opening in said solution container when said receiving member engages the twist-off member and said applicator head is rotated relative to said solution container.

28. A solution applicator comprising:
   a solution container having a twist-off member that enables solution in said solution container to flow out of the solution container when said twist-off member is twisted; and
   an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container to enable fluid to flow from said solution container through the solution pathway and through the aperture in said applicator head;
   wherein said solution container has a locating pin that protrudes outwardly from said solution container, and said applicator head has a slot near its proximal end that is engaged by the locating pin to ensure proper orientation of said applicator head as it is coupled to said solution container.

29. The solution applicator of claim 28 wherein said twist-off member is connected to the solution container by a frangible web unitary with the twist-off member and said solution container.

30. A solution applicator comprising:
   a solution container having a twist-off member that enables solution in said solution container to flow out of the solution container when said twist-off member is twisted, wherein said solution container comprises a container portion connected to a cap to form a sealed reservoir of solution inside of said solution container, said cap having the twist-off member, wherein said twist-off member is connected to the cap of said solution container by a frangible web unitary with the twist-off member and the cap; and
   an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container at the twist-off member to enable fluid to flow from said solution container through the solution pathway and through the aperture in said applicator head.

31. The solution applicator of claim 30 wherein said frangible web is formed of a thinner material than the rest of said solution container so that the frangible web tears to form an opening in said solution container when said receiving member engages the twist-off member and said applicator head is rotated relative to said solution container.

32. A solution applicator comprising:
   a solution container having a twist-off member that enables solution in said solution container to flow out of the solution container when said twist-off member is twisted, wherein said solution container comprises a container portion connected to a cap to form a sealed reservoir of solution inside of said solution container, said cap having the twist-off member, wherein said solution container and said applicator head each have indicia thereon, said indicia are positioned so that when they line up upon rotation of said applicator head relative to said solution container, the twist-off member has been torn to create an opening in said solution container; and an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container at the twist-off member to enable fluid to flow from said solution container through the solution pathway and through the aperture in said applicator head.

33. The solution applicator of claim 32 wherein said twist-off member is connected to the solution container by a frangible web unitary with the twist-off member and said solution container.

34. A solution applicator comprising:

a solution container having a twist-off member that enables solution in said solution container to flow out of the solution container when said twist-off member is twisted, wherein said solution container comprises a container portion connected to a cap to form a sealed reservoir of solution inside of said solution container, said cap having the twist-off member, wherein the cap has a locating pin that protrudes outwardly from the cap, and said applicator head has a slot near its proximal end that is engaged by the locating pin to ensure proper orientation of said applicator head as it is coupled to said solution container; and an applicator head having a proximal end and a distal end and a solution pathway extending from the proximal end to the distal end, said applicator head engaged with said solution container at the proximal end, said applicator head having an aperture at the distal end, and said applicator head having a receiving member that the twist-off member engages when said applicator head is rotated relative to said solution container to thereby open said solution container to enable fluid to flow from said solution container through the solution pathway and through the aperture in said applicator head.

35. The solution applicator of claim 34 wherein said twist-off member is connected to the solution container by a frangible web unitary with the twist-off member and said solution container.

* * * * *